(12) United States Patent
Short et al.

(10) Patent No.: US 8,929,620 B2
(45) Date of Patent: Jan. 6, 2015

(54) METHOD AND APPARATUS FOR SIMULTANEOUS ACQUISITION OF MULTIPLE EXAMINATION DATA

(75) Inventors: Stephanie A. Short, Mukwonago, WI (US); Mohamed Ali Hamadeh, Waukesha, WI (US); Sundar Swamy, Bangalore (IN); Anil Issac, Banaglaore (IN); Renuka Uppaluri, Pewaukee, WI (US); Renaud B. Maloberti, Pewaukee, WI (US); Jianqing Yao, Rochester, NY (US); Lloyd W. Ison, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 2194 days.

(21) Appl. No.: 10/286,673

(22) Filed: Nov. 1, 2002

(65) Prior Publication Data

US 2004/0086202 A1    May 6, 2004

(51) Int. Cl.
  *G06K 9/00*   (2006.01)
  *G06F 19/00*  (2011.01)
  *G06Q 50/22*  (2012.01)

(52) U.S. Cl.
  CPC .............. *G06F 19/321* (2013.01); *G06Q 50/22* (2013.01)
  USPC .................... 382/128; 382/131; 705/2; 705/3

(58) Field of Classification Search
  USPC ............ 705/2, 3; 378/108; 600/407; 382/131
  See application file for complete search history.

(56) References Cited

U.S. PATENT DOCUMENTS

| 5,722,405 | A  | * | 3/1998  | Goldberg ........................ 600/407 |
| 6,210,327 | B1 | * | 4/2001  | Brackett et al. ................ 600/437 |
| 6,263,228 | B1 | * | 7/2001  | Zhang et al. ................... 600/409 |
| 6,440,072 | B1 | * | 8/2002  | Schuman et al. ............... 600/437 |
| 6,603,494 | B1 | * | 8/2003  | Banks et al. ................... 715/807 |
| 6,718,192 | B1 | * | 4/2004  | Samara et al. ................. 382/128 |
| 6,836,558 | B2 | * | 12/2004 | Doi et al. ....................... 382/131 |
| 7,099,499 | B2 | * | 8/2006  | Blezek et al. .................. 382/128 |
| 2003/0165216 | A1 | * | 9/2003 | Walker et al. .................. 378/108 |
| 2004/0068167 | A1 | * | 4/2004 | Hsieh et al. .................... 600/407 |
| 2004/0077952 | A1 | * | 4/2004 | Rafter et al. ................... 600/481 |

FOREIGN PATENT DOCUMENTS

| JP | 200213393  | 5/2002 |
| JP | 2002279395 | 9/2002 |

* cited by examiner

*Primary Examiner* — Michael Fuelling
(74) *Attorney, Agent, or Firm* — Fletcher Yoder, P.C.

(57) ABSTRACT

Disclosed is an image acquisition workstation including a multiple examination mode. In the multiple examination mode, a user selects an anatomical view or procedure prior to acquiring data. When the image data is acquired, the acquired data is stored in a data structure related to the selected procedure or anatomical view. As the user selects a procedure or anatomical view prior to each data acquisition, the image acquisitions can be acquired in any order.

13 Claims, 4 Drawing Sheets

METHOD AND APPARATUS FOR SIMULTANEOUS ACQUISITION OF MULTIPLE EXAMINATION DATA

CROSS-REFERENCE TO RELATED APPLICATION

None.

STATEMENT REGARDING FEDERALLY SPONSORED RESEARCH OR DEVELOPMENT

None.

BACKGROUND OF THE INVENTION

Computer networks employed in hospitals and particularly hospital radiology departments typically include a Hospital (or Radiology) Information System (HIS) for entering and storing patient and procedure data, an acquisition workstation for controlling image acquisition equipment, and a Picture Archival and Communication System (PACS) for archiving the acquired image data along with other information such as billing data. In use, patient data and required imaging procedures are typically entered into the HIS system and are downloaded or otherwise transmitted to the acquisition workstation. Alternatively, or in addition to the entries at the HIS, the patient data can be entered directly into or edited at the workstation. After the data is entered images are acquired at the workstation, and the acquired data is transmitted to the PACS for archiving and storage.

In these systems, each imaging procedure is associated with a particular anatomical view of the patient, and procedures are performed in a sequential procedure to procedure basis. As images are acquired they are therefore typically stored in a data structure based on the anatomical view. This method of data storage is advantageous in that the collected data is categorized appropriately for data acquisition, for review of acquired data by a radiologist, and for billing purposes. Furthermore, the data structures associated with the HIS, workstation, and PACS systems are typically all based on anatomical views for organization. This method of organization simplifies the maintenance of the integrity of data across multiple nodes in the network or other system by maintaining a defined data structure across all nodes of the network.

While present methods of data acquisition and organization are therefore advantageous for storage, retrieval, and maintenance purposes, there are disadvantages associated with these methods. For example, because each procedure is tied to a particular anatomical view, anatomical views must be acquired sequentially at the acquisition workstation to assure that image data sets are associated with the appropriate anatomical view. If, for example, both a chest and hip view are required, all images of the hip are acquired first and, then, all views of the chest are acquired. This method requires frequent repositioning of the patient, which is time consuming and can be uncomfortable for the patient. Furthermore, once a list of procedures is established, it is typically not possible to add additional procedures and therefore acquire additional anatomical views after the acquisition process has begun. Additionally, when errors occur in data acquisition, there is typically no method for correcting these errors before the image data is downloaded to the PACS system, however, it can be difficult and time consuming to re-map this data. Typical acquisition systems are therefore not optimally efficient in terms of workflow and speed.

SUMMARY OF THE INVENTION

In one aspect, the present invention comprises a method for acquiring and organizing image data resulting from multiple acquisitions performed by an image acquisition computing device. In this method, a list of imaging procedures for obtaining images of an anatomical view are displayed. The user selects an imaging procedure from the list of imaging procedures, and acquires an image data set for producing an image associated with the selected imaging procedure, such that the image data set is correlated with the anatomical view. The user continues to select an anatomical view to associate the acquired data with prior to each data acquisition until image data sets are acquired for reconstructing images of a selected set of anatomical views from the list of imaging procedures.

In another aspect of the invention, an error correcting tool is provided, wherein the user can selectively move image data associated with an acquisition from a first procedure to a second procedure, thereby allowing correction of imaging data prior to archiving.

Another aspect of the present invention is an imaging acquisition workstation. The imaging acquisition workstation includes a multiple exam mode, in which a user can select a procedure for which data is to be acquired, and then acquire an image data set associated with that procedure. In successive image data acquisitions, therefore, image acquisition data for different procedures can be obtained, thereby avoiding the need to sequentially obtain image data for a given procedure.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE PREFERRED EMBODIMENT

Figure 1:
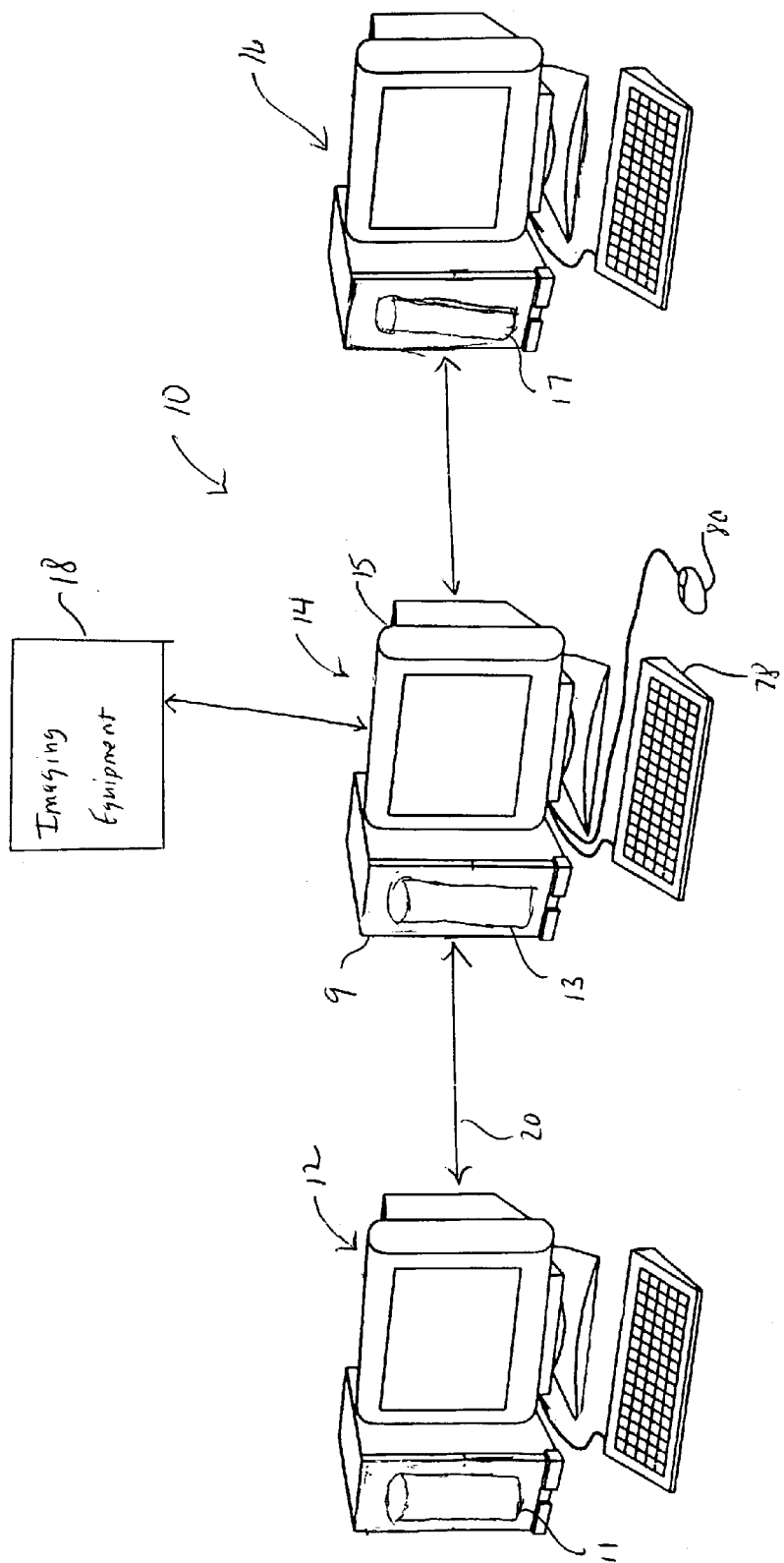
FIG. 1 is a block diagram of a hospital network system including an acquisition workstation.

Referring now to the Figures and more particularly to FIG. 1, a hospital computer network 10 is shown. The computer network 10 includes a hospital or radiology information system (HIS) 12 including a database stored in memory 11, an image acquisition workstation 14 linked to imaging equipment 18 and including a database stored in memory 13, and a picture archive and communications system (PACS) 16 for archiving acquired images and associated data in memory 17. The HIS 12, acquisition workstation 14, and PACS 16 are linked via a communications network 20 which can be, for example, an intranet link, hard wired network, wireless network, or other types of communications links well know to those of skill in the art.

In operation, the HIS 12 is typically located at a front desk, and is operated by an administrator who is responsible for entering patient data. The acquisition workstation 14 is typically provided in an examination room or area, and, as noted above, is coupled to medical imaging equipment 18 to provide imaging commands to the medical imaging equipment 18 and to acquire and reconstruct image data. Upon close of an examination, acquired data is transmitted to the PACS 16 for storage. To allow for flexibility in image acquisition procedure, the workstation includes both a single exam mode which provides a sequential procedure by procedure data acquisition as found in typical prior art systems, and a multiple exam mode, in which the technician operating the equipment can select the image data to be acquired in any order, as described below, and store the acquired data in association with a selected anatomical view. Furthermore, the workstation 14 provides a tool for moving image data from one data structure to another, and therefore to correct errors which occur in characterizing data prior to archiving the data. Additionally, while in the multiple exam mode the workstation also provides a tool for allowing the technician to add procedures to the exam.

Figure 2:
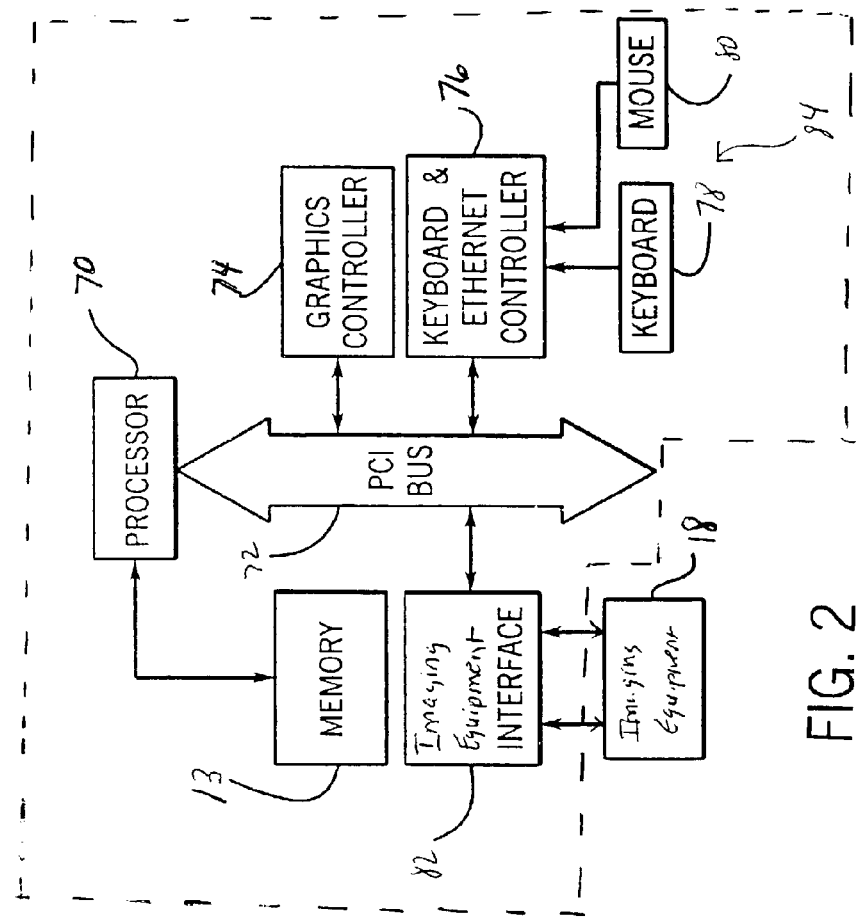
FIG. 2 is a block diagram of a workstation for use in a hospital computer system of FIG. 1.

Referring now to FIGS. 1 and 2 the workstation 14 includes a case 9 which houses the processor 70 and associated circuitry, memory 13, and peripheral interface circuits including a commercially available CRT monitor or display 15, and a user input device 84 which can include, as shown, both a keyboard 78 and mouse 80. The workstation 14 includes an imaging equipment interface 82 which is connected to imaging equipment 18 both to control the imaging equipment 18 and to receive digitized image data directly from the medical imaging equipment 18. The imaging equipment can be, for example, an x-ray system, x-ray CT system, MRI system, PET scanner system or nuclear medicine system. The workstation 14 also typically contains application programs which perform image processing functions, such as, filtering the medical image data, transforming the size and orientation of the medical images and adding textual information to the medical images.

Referring particularly to FIG. 2, the workstation 14 includes a processor 70 which executes instructions stored in a memory 13. The processor 70 can be, for example, a commercially available RISC processor which includes an integral PCI bus driver to provide a direct interface with a PCI bus 72 and integral memory management circuitry for handling all external memory 13 such as are available from Sun Microsystems, Inc. Other types of processors and related hardware systems will be apparent to those of ordinary skill in the art.

The PCI bus 72 is an industry standard bus that transfers data between the processor 70 and a number of peripheral controller cards. These include a network controller 76 which supports data transfer with peripheral devices, including input from the keyboard 78 and mouse 80 and an imaging equipment interface 18 which communication with network ports on medical imaging equipment 18. The workstation 14 further includes a graphics controller 74 coupled to the PCI bus 72 and to the display or monitor 15 through a connection such as a standard VGA connection (not shown). As noted above, the workstation 14 application software stored in the memory 13 includes one or more software switch for selectively providing both a single acquisition mode and a multiple acquisition mode, as described more fully below.

Referring particularly to FIG. 2, medical images are input to the workstation 14 through a network link such as an Ethernet link associated with the imaging equipment interface 82. The image data is downloaded to the workstation through the imaging equipment interface 82 and stored in memory 13, where a number of image processing functions known to those of skill in the art may be performed on the image data.

Figure 3:
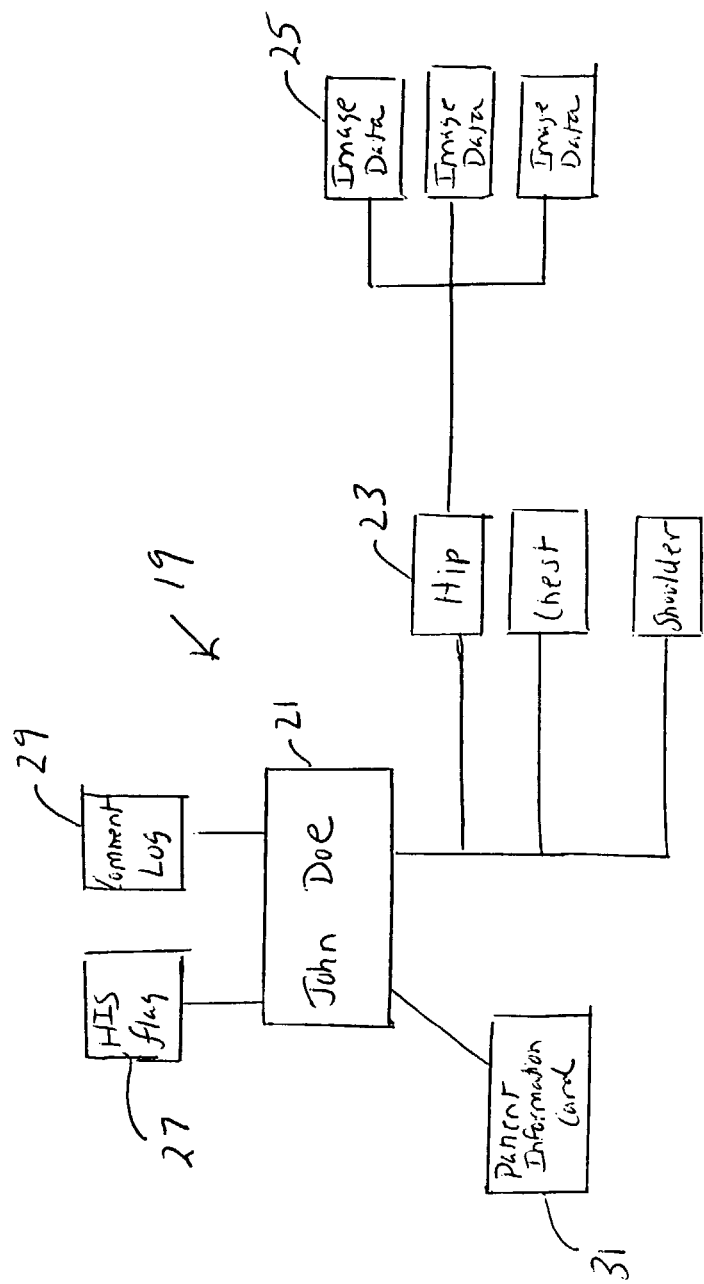
FIG. 3 is a block diagram of a patient data structure.

Referring now to FIG. 3, the acquired image data is preferably stored in a patient data structure 19 in the memory 13 of the workstation 14. In one embodiment, the patient data structure 19 comprises a hierarchical structure or "folder", in which the highest level is a patient identifier 21. The patient identifier 21 typically comprises a patient name, although a social security number, phone number, accession number, or other identifying data could also be used. Beneath the top level, data related to the identified patient, including imaging or other medical procedures 23 to be performed on the subject is stored. As the results of medical procedures 23 performed on the patient are acquired, this acquisition data 25 is also stored in the patient data structure 19, typically at a level beneath the procedure. Also associated with the patient data structure 19 is a flag 27, which is set when the patient data structure 19 has been entered at the HIS 12, to allow the workstation 14 to differentiate between data entered locally and data entered at the HIS 12. The patient data structure 19 also includes a log 29 where comments related to changes in the structure can be provided. While the data structure 19 illustrates one method of organizing data, it will be apparent that there are many alternate ways of organizing patient data. Furthermore, while the patient data structure 19 is described with reference to the workstation 14, a similar patient data structure 19 is preferably provided at each of the HIS 12, workstation 14, and PCS 16 to maintain data integrity across the hospital computer network 10.

Figure 4:
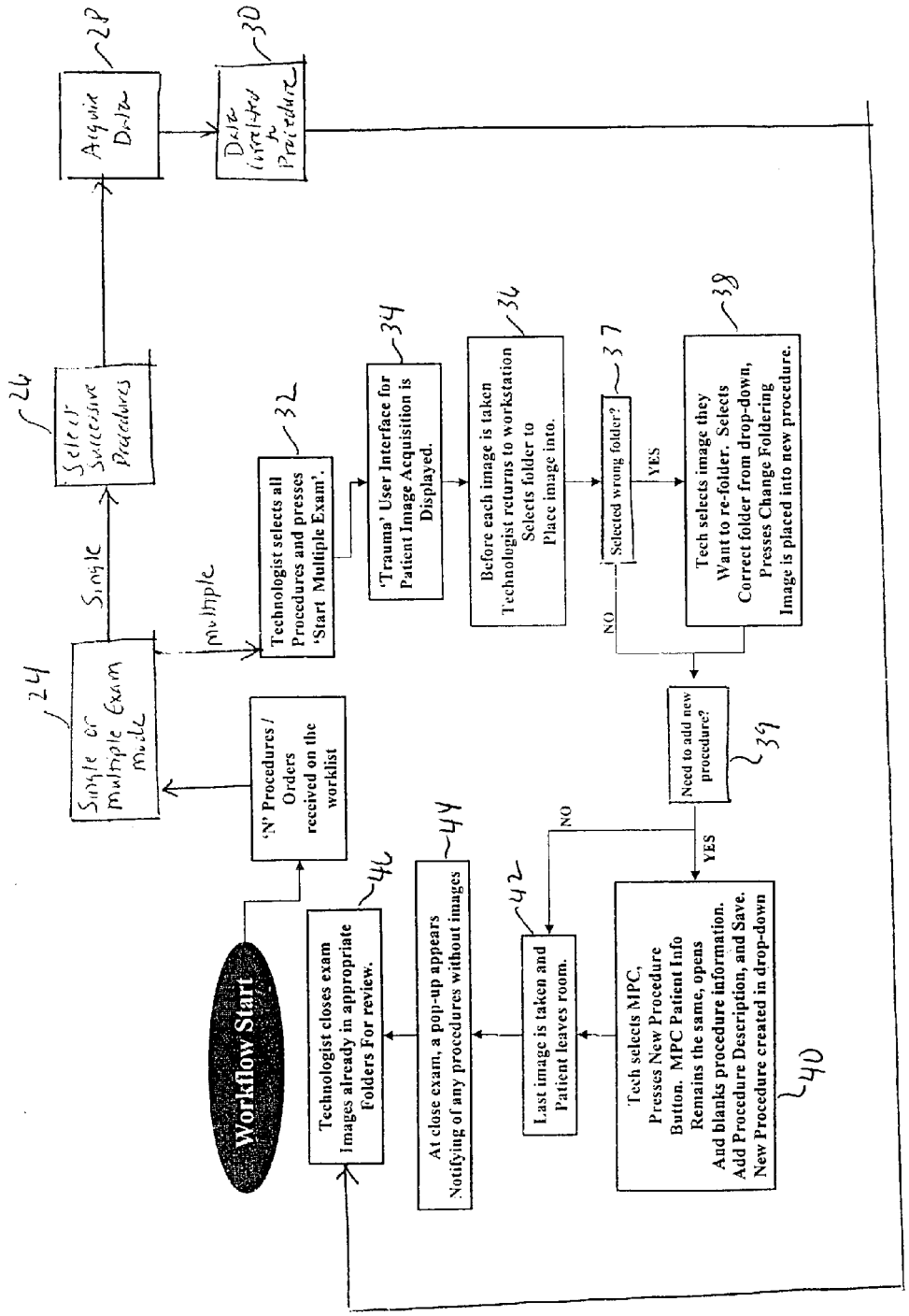
FIG. 4 is a flow chart illustrating a workflow at the acquisition workstation of FIG. 1.

Referring now to FIG. 4, a workflow chart illustrating a data acquisition procedure for the acquisition workstation 14 is shown. In step 22, a worklist including a pre-defined set of imaging procedures required for the patient is shown. The worklist data, as noted above, could have been entered into the HIS system 12 or entered directly into the acquisition workstation 14 as local data before the acquisition is started. Having reviewed the worklist, in step 24, the technician can select between a single exam mode, wherein in steps 26, 28, and 30, each imaging procedure in the patient data structure 19 is activated successively, and data is acquired and stored in the associated procedure or anatomical view. This selection is particularly useful when the worklist include only a single procedure 23.

Alternatively in step 24, the technician can select a multiple exam mode, and proceed to step 32, wherein the technician selects either all of the imaging procedures for the acquisition or a subset of imaging procedures. In step 34, a "trauma" user interface allows the technician to select among the various procedures 23 (FIG. 3) to receive data from the first acquisition.

Referring now to FIGS. 3 and 4, in step 36, the technician selects a procedure 23 for receiving data from the next image acquisition. Thus, for example, if the next image to be acquired is an image data set associated with the hip, the technician selects a procedure 23 associated with hip images. The image data set is then acquired, and is stored as acquisition data 25 under the selected procedure 23. In step 37, the technician reviews the selected procedure 23 and determines whether the placement is correct. If not, in step 38, the technician selects the image to be moved to a different procedure 23, chooses the procedure 23 the image is to be moved to, and selects a "change folder" tool, wherein the image is moved to the new procedure 23.

If the image data set was placed in the correct folder and/or if the image data set has been moved, in step 39, the technician reviews the imaging folder list to determine an additional procedure is required. If so, in step 40, the technician selects a "new procedure" tool for entering a new procedure 23 is displayed. This selection can be made at any time, including during acquisition. The technician enters the information into for the new procedure 23 in the form, and saves the form, wherein another procedure 23 is provided to which acquired image data sets can be added. Image acquisition can thereafter proceed until, as shown in step 42, the last image data set is acquired and the technician signals the acquisition workstation 14 that the exam is closed. At step 44, the acquisition workstation 14 reviews the procedures 23 to determine if any are empty and, if so, a notice is provided on the display 15, indicating to the technician which procedures have no images associated therewith. At this point the technician can restart the exam to take additional images, or determine that no images are required in the empty procedures 23. At the close of the procedure, in step 46, the images are in appropriate order for review by a radiologist, and can be forwarded to the PACS 16 for archiving.

The acquisition workstation 14 as described allows for the acquisition of multiple images, in any order by the technician, thereby increasing the efficiency of the acquisition procedure, and minimizing movement and discomfort of the subject. Furthermore, the system allows for the addition of imaging procedures that were not included in the original request. At the completion of the procedure, the acquired data is provided in a data structure in which the image data is categorized appropriately before the images are archived in the PACS 10. The workstation also allows image data to be moved to the correct folder, again before the data is provided to the PACS. which allows for easy and efficient analysis by a radiologist or other medical personnel. The system is also useful in trauma situations, in that it allows a number of images of a patient to be acquired quickly and with minimal movement, and further provides for storage of the data under a "trauma interface", in which data can be stored with minimal identifying data.

It should be understood that the methods and apparatuses described above are only exemplary and do not limit the scope of the invention, and that various modifications could be made by those skilled in the art that would fall under the scope of the invention. To apprise the public of the scope of this invention, the following claims are made:

The invention claimed is:

1. A method for acquiring and organizing image data comprising:
   (a) selecting multiple different imaging procedures for imaging multiple different anatomies of a subject from a list of different imaging procedures to associate with respective multiple image data sets;
   (b) selecting multiple different folders in which to place respective multiple image data sets from the selected multiple different imaging procedures;
   (c) acquiring the multiple different image data sets by performing the selected multiple different imaging procedures;
   (d) reviewing the acquired multiple different image data sets from the respective the selected multiple different imaging procedures and associating the acquired multiple different image data sets with the corresponding selected multiple different imaging procedures by moving at least one of the acquired multiple different image data sets from one folder to another folder; and
   (e) repeating at least steps (c)-(d) until multiple different image data sets are acquired for reconstructing an image associated with each of the selected multiple different imaging procedures, wherein each of the multiple different image data sets are stored in one of the folders.

2. The method as defined in claim 1, further comprising:
   (f) selectively adding additional different imaging procedures to the list of different imaging procedures and selectively acquiring different image data sets for the additional different imaging procedures.

3. The method as defined in claim 1, wherein step (a) includes selecting acquisition of an image data set in a single exam mode in which an order of acquisition of the image data set is predetermined.

4. The method as defined in claim 1, further comprising: comparing the multiple different image data sets to each of the selected multiple different imaging procedures and notifying a user if no image data sea exists for any selected imaging procedure.

5. The method as defined in claim 1, wherein step (a) includes selection of acquisition of image data sets for multiple different imaging procedures in which an order of acquisition of the image data sets is selectable.

6. An image acquisition and organization method executed by non-transitory programming on computing device, the method comprising:
   displaying a list of multiple different imaging procedures for acquiring multiple different image data sets of multiple different body parts of a subject; and
   acquiring the image data sets;
   wherein an order of acquisition of the image data sets for each of the multiple different image data sets is selectable by a user and the image data is automatically correlated with the multiple different imaging procedures; and
   wherein each of the multiple different image data sets is selectively associated with one of the imaging procedures prior to acquisition of the respective image data set and is selectively moveable to be associated with another of the multiple different imaging procedures after acquisition of the respective image data set.

7. The method as defined in claim 6, further comprising verifying that at least one of the multiple different image data sets is associated with each of the multiple different imaging procedures before an imaging examination is closed.

8. The method as defined in claim 6, further comprising adding at least one additional different imaging procedure to the list of multiple different imaging procedures.

9. An imaging system comprising:
   an imaging acquisition device; and
   an image acquisition workstation coupled to the imaging acquisition device;
   wherein the image acquisition workstation is programmed via non-transitory programming for selecting multiple different imaging procedures for imaging multiple different body parts of a subject to be started and performed simultaneously from a worklist of the multiple different imaging procedures at the image acquisition workstation; and
   wherein each of the multiple different imaging procedures is for a single image acquisition of the multiple different body parts of the subject being imaged.

10. The system of claim 9, wherein the non-transitory programming of the image acquisition workstation provides for adding new different imaging procedures to the worklist of multiple different imaging procedures at the image acquisition workstation.

11. The system of claim 9, wherein the non-transitory programming of the image acquisition workstation provides for storing image data sets acquired from the multiple different imaging procedures in folders corresponding to the multiple different imaging procedures.

12. The system of claim 11, wherein the non-transitory programming of the image acquisition workstation provides for moving images between different folders.

13. A method for acquiring medical images from a medical imaging system comprising:
- selecting multiple different imaging procedures for imaging multiple different body parts of a subject from a worklist of multiple different imaging procedures listed on an image acquisition workstation;
- starting the selected multiple different imaging procedures on the subject simultaneously to acquire respective image data sets;
- adding new different imaging procedures for the subject currently undergoing an imaging procedure; and
- storing the image data sets acquired from the multiple different imaging procedures in multiple different folders corresponding to the multiple different imaging procedures;
- wherein each of the multiple different imaging procedures is for image acquisition of a respective one of the multiple different body parts of the subject being imaged.

\* \* \* \* \*